US 12,357,448 B2

(12) United States Patent
Verma et al.

(10) Patent No.: US 12,357,448 B2
(45) Date of Patent: Jul. 15, 2025

(54) TENSIONABLE KNOTLESS ANCHORS AND METHODS OF TISSUE REPAIR

(71) Applicant: Arthrex, Inc., Naples, FL (US)

(72) Inventors: Nikhil N. Verma, Chicago, IL (US); Justin W. Griffin, Virginia Beach, VA (US); Michael J. Huang, Colorado Springs, CO (US); Asheesh Bedi, Ann Arbor, MI (US); Andrew C. Petry, Naples, FL (US); Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 525 days.

(21) Appl. No.: 17/113,499

(22) Filed: Dec. 7, 2020

(65) Prior Publication Data

US 2022/0175514 A1 Jun. 9, 2022

(51) Int. Cl.
*A61F 2/08* (2006.01)
*A61B 17/04* (2006.01)

(52) U.S. Cl.
CPC ........ *A61F 2/0811* (2013.01); *A61B 17/0469* (2013.01); *A61B 2017/0464* (2013.01); *A61B 2017/0475* (2013.01); *A61B 2017/0496* (2013.01); *A61F 2002/0852* (2013.01)

(58) Field of Classification Search
CPC ........ A61B 2017/0475; A61B 17/0401; A61B 17/0485; A61F 2/0811; A61F 2002/0847
See application file for complete search history.

(56) References Cited

U.S. PATENT DOCUMENTS

| 5,312,423 A | 5/1994 | Rosenbluth et al. |
| 5,797,928 A | 8/1998 | Kogasaka |
| 8,956,372 B2 | 2/2015 | Fenton et al. |
| 9,737,293 B2 * | 8/2017 | Sengun ............ A61B 17/06166 |
| 11,224,417 B2 * | 1/2022 | Nason ................ A61B 17/0401 |
| 2008/0255613 A1 * | 10/2008 | Kaiser .............. A61B 17/06166 606/232 |

(Continued)

FOREIGN PATENT DOCUMENTS

| EP | 1908424 B1 | 7/2016 |
| JP | 2018509225 A | 4/2018 |

(Continued)

OTHER PUBLICATIONS

International Search Report and Written Opinion dated Dec. 6, 2021, issued in International Application No. PCT/US2021/046829.

(Continued)

*Primary Examiner* — Brian A Dukert
(74) *Attorney, Agent, or Firm* — Potomac Law Group, PLLC

(57) ABSTRACT

Tensionable, knotless, self-locking surgical constructs and methods for surgical repairs are disclosed. A tensionable, knotless, self-locking surgical construct includes two self-locking, tensionable, knotless independent mechanisms loaded onto a fixation device, one of the two self-locking, tensionable, knotless, independent mechanisms including a preformed, flexible, continuous, uninterrupted loop. The fixation device can be a knotless fixation device such as a hard-body anchor, or a knotless soft anchor such as an all-suture knotless anchor.

9 Claims, 5 Drawing Sheets

(56) References Cited

U.S. PATENT DOCUMENTS

| | | | |
|---|---|---|---|
| 2009/0036905 A1* | 2/2009 | Schmieding | A61B 17/0401 |
| | | | 606/232 |
| 2009/0082805 A1* | 3/2009 | Kaiser | A61B 17/06166 |
| | | | 606/228 |
| 2009/0088781 A1 | 4/2009 | Prestel et al. | |
| 2012/0165864 A1* | 6/2012 | Hernandez | A61B 17/0401 |
| | | | 606/232 |
| 2013/0190818 A1* | 7/2013 | Norton | A61B 17/0401 |
| | | | 606/232 |
| 2013/0267999 A1* | 10/2013 | Ng | A61B 17/1615 |
| | | | 606/232 |
| 2013/0345749 A1 | 12/2013 | Sullivan et al. | |
| 2014/0249577 A1 | 9/2014 | Pilgeram | |
| 2015/0032157 A1 | 1/2015 | Dooney, Jr. et al. | |
| 2015/0051644 A1 | 2/2015 | Holmes | |
| 2015/0297211 A1* | 10/2015 | Sullivan | A61B 17/0401 |
| | | | 606/232 |
| 2017/0049434 A1* | 2/2017 | Dooney, Jr. | A61B 17/0401 |
| 2017/0189007 A1* | 7/2017 | Burkhart | A61B 17/0401 |
| 2018/0221010 A1 | 8/2018 | Lund | |
| 2018/0310930 A1 | 11/2018 | Nason et al. | |
| 2020/0022694 A1 | 1/2020 | Burkhart et al. | |
| 2020/0275922 A1 | 9/2020 | Valentin et al. | |

FOREIGN PATENT DOCUMENTS

| | | | | |
|---|---|---|---|---|
| JP | 2020523112 A | 8/2020 | | |
| WO | WO-2020047431 A2 * | 3/2020 | | A61B 17/06166 |

OTHER PUBLICATIONS

Extended European Search Report for European Application No. 20763326 dated Oct. 21, 2022.

Extended European Search Report for European Application No. 21904039.1 dated Feb. 22, 2024.

Office Action for Japanese Patent Application No. 2023-534321 issued on Jan. 28, 2025 (includes English language translation).

* cited by examiner

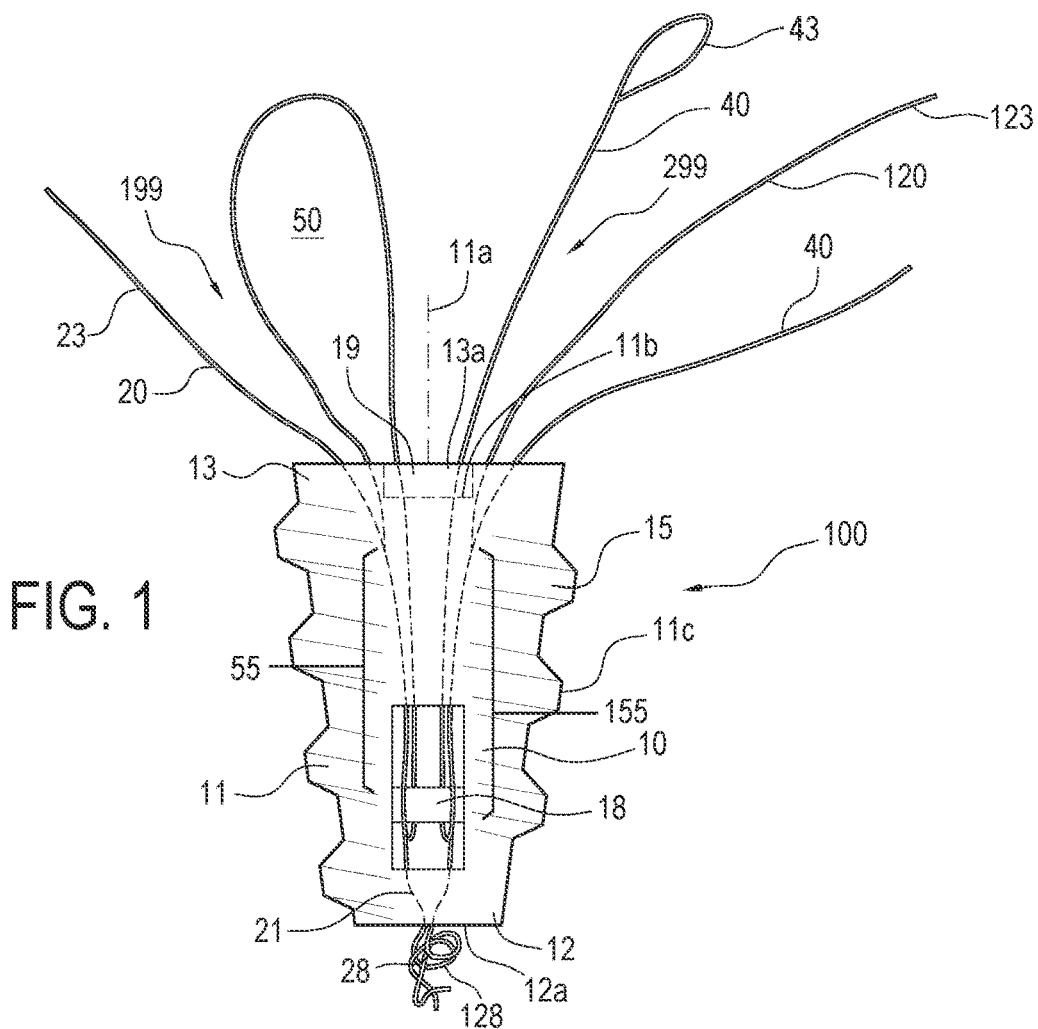
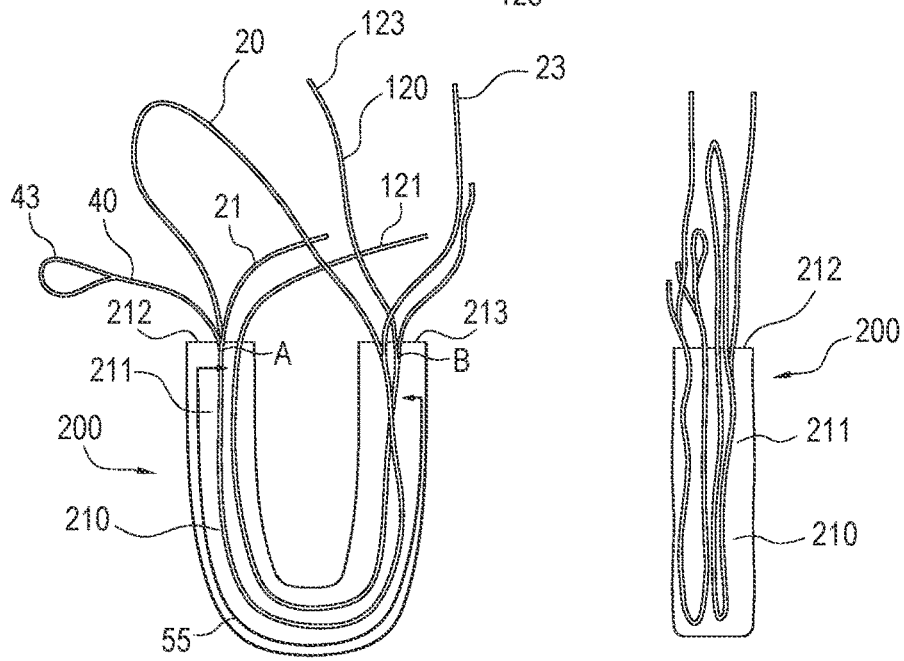
FIG. 1   FIG. 2   FIG. 3

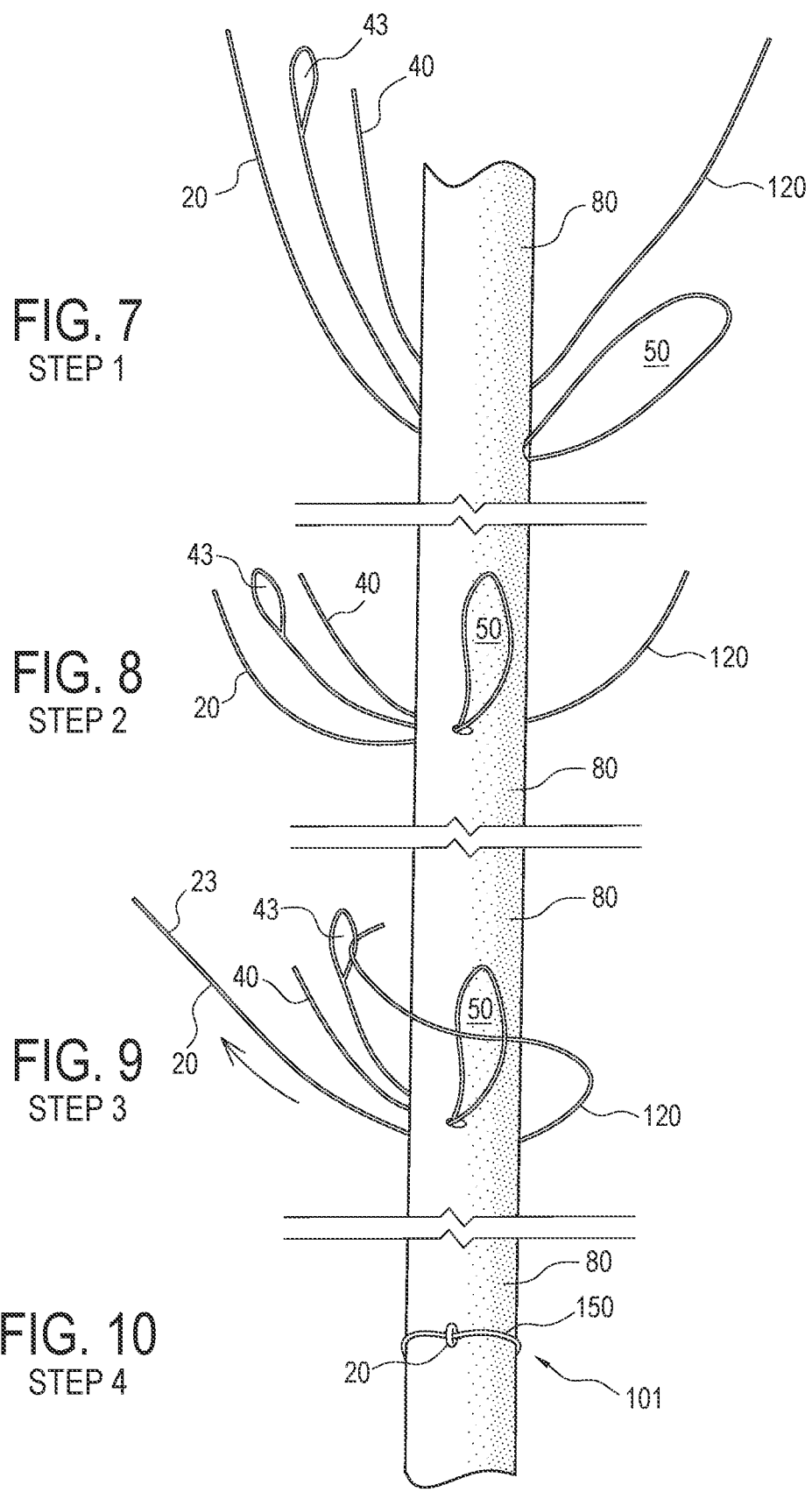

FIG. 15
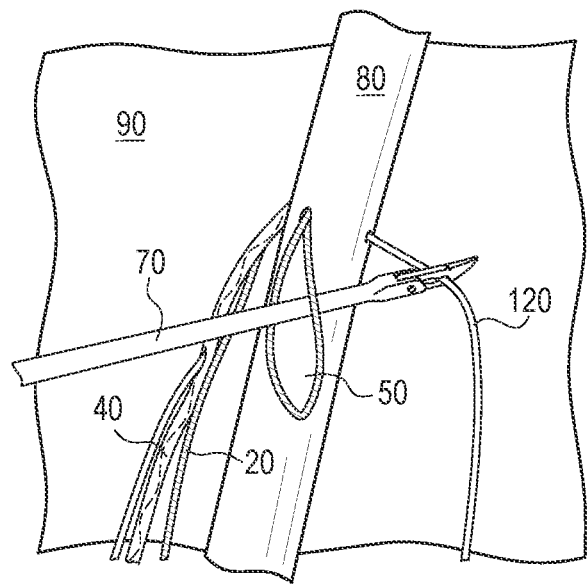
FIG. 16
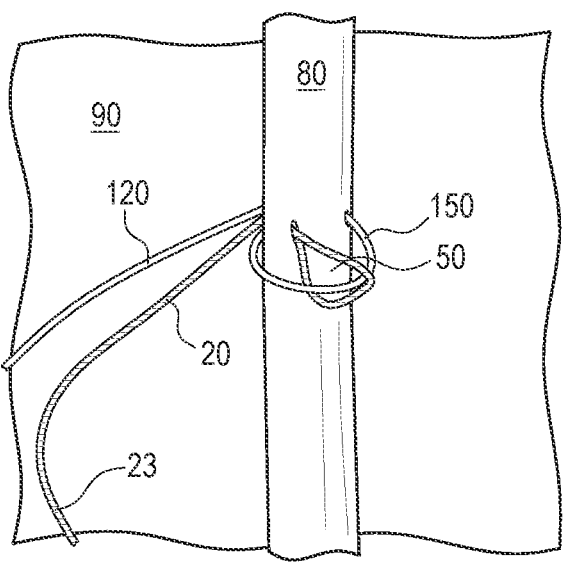
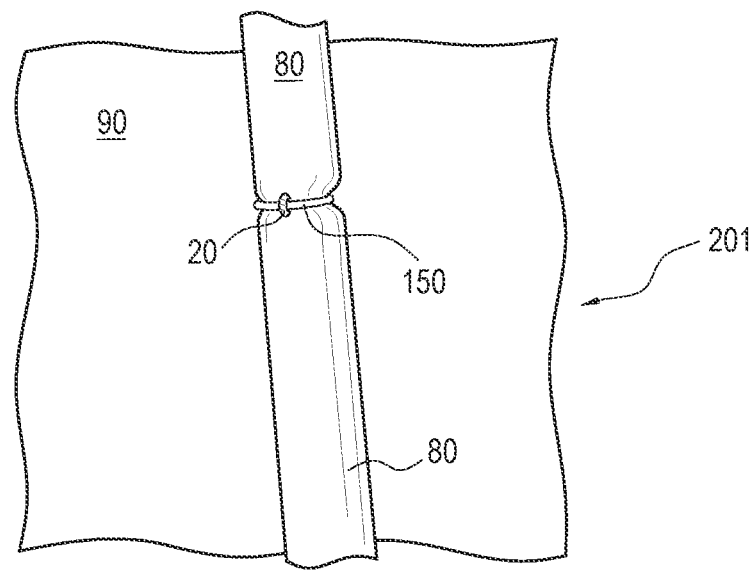
FIG. 17

TENSIONABLE KNOTLESS ANCHORS AND METHODS OF TISSUE REPAIR

BACKGROUND

The disclosure relates to the field of surgery and, more specifically, to knotless anchor constructs and associated methods of tissue repairs.

SUMMARY

Reconstruction systems, assemblies, kits, and methods for fixation of soft tissue are disclosed.

A tensionable, knotless surgical construct can create a knotless, self-locking, reinforced repair. A tensionable, knotless, self-locking surgical construct includes two self-locking, tensionable, knotless independent mechanisms loaded onto a fixation device, one of the two tensionable mechanisms including a preformed, flexible, continuous, uninterrupted loop. The fixation device can be a knotless fixation device such as a hard-body anchor, or a knotless soft anchor such as an all-suture knotless anchor. The knotless surgical construct may be employed in knotless fixation of first tissue to second tissue, for example, fixation of tendon to bone.

Methods of tissue repairs are also disclosed. In an embodiment, a knotless surgical construct provides soft tissue to bone fixation without any knot formation, with fewer passing steps, and with increased fixation and soft tissue compression.

BRIEF DESCRIPTION OF THE DRAWINGS

FIG. 1 illustrates a cross-sectional view of a surgical construct according to an exemplary embodiment.

FIG. 2 illustrates a schematic front view of a surgical construct according to another exemplary embodiment.

FIG. 3 illustrates a side view of surgical construct of FIG. 2.

FIGS. 7-10 illustrate schematic steps of a tissue repair with the surgical construct of FIG. 6.

FIGS. 11-17 illustrate an exemplary method of tissue repair with the surgical construct of FIG. 1.

DETAILED DESCRIPTION

Figure 4:
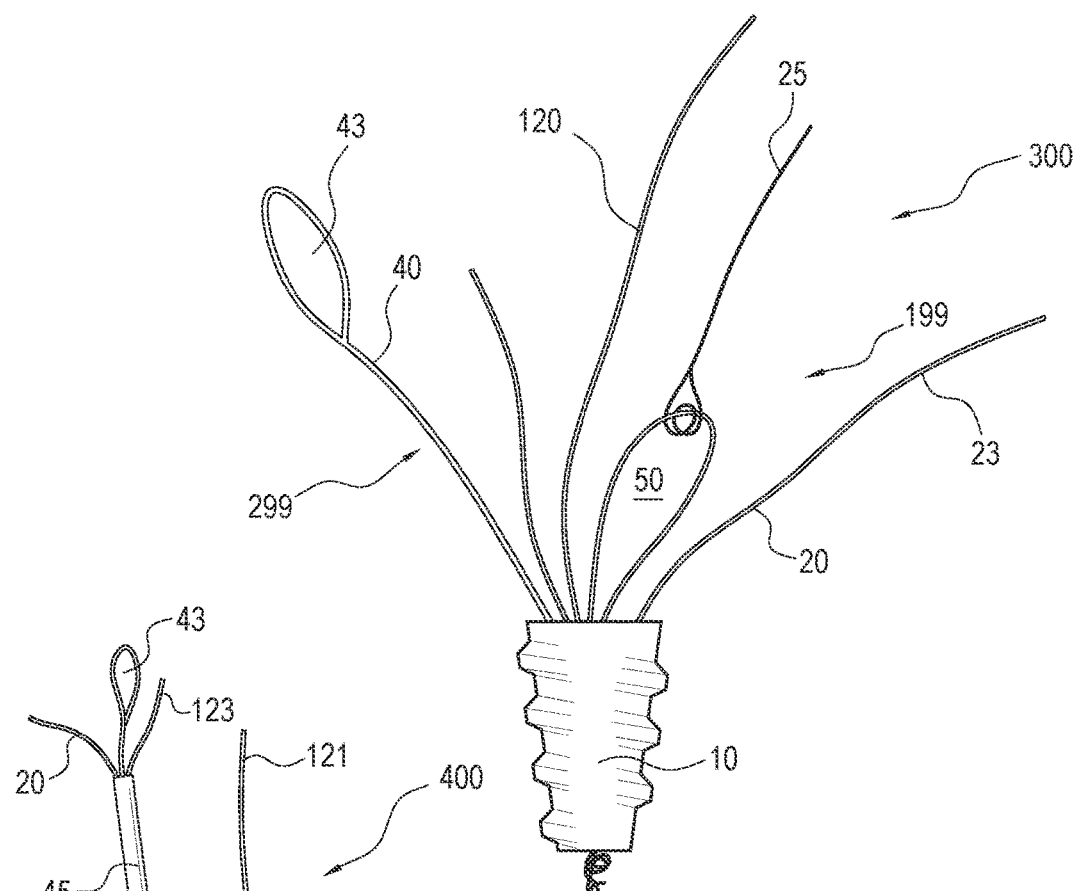
FIG. 4 illustrates a schematic view of a surgical construct according to another exemplary embodiment.

A tensionable, knotless, self-cinching, self-locking surgical construct can create a knotless, reinforced repair.

A soft tissue repair system includes a tensionable, knotless, self-locking surgical construct with two self-locking, tensionable, knotless, independent mechanisms loaded onto a fixation device, at least one of the two self-locking, tensionable, knotless, independent mechanisms including a flexible coupler with a preformed continuous, uninterrupted loop. The fixation device can be a knotless fixation device such as a hard-body anchor, or a soft anchor such as an all-suture knotless anchor. The knotless surgical construct may be employed in knotless fixation of first tissue to second tissue, for example, fixation of soft tissue to bone.

Methods of knotless tissue repairs are also disclosed. In an embodiment, a surgical construct provides knotless soft tissue to bone fixation, without any knot formation, with fewer passing steps, and with increased fixation and soft tissue compression. The methods allow formation of Loop 'N' Tack™ repairs of tendon to bone, with increased strength and tendon compression. In an embodiment, a first tissue is approximated to a second tissue with a knotless, tensionable, self-locking, surgical construct that includes two tensionable, self-locking mechanisms loaded onto a fixation device. One of the two self-locking mechanisms includes a flexible coupler with a continuous, uninterrupted, preformed loop. The other of the two self-locking mechanisms includes a shuttling device attached to another flexible coupler (a repair suture).

The disclosure provides surgical self-locking knotless surgical constructs, systems and assemblies, as well as methods for securing a first tissue to a second tissue, for example, knotless fixation of soft tissue (ligament, tendon, graft, etc.) to bone. The self-locking knotless surgical construct includes a fixation device with two tensionable constructs (two self-locking mechanisms) which form two knotless, flexible, closed, intertwined loops around the soft tissue to be secured to the bone.

Fixation devices (tensionable knotless anchors) are inserted into bone with two suture mechanisms (two tensionable constructs) formed of first and second flexible couplers provided within the fixation device and a shuttle/pull device (a suture passing instrument) attached to one of the flexible couplers (for example, the second flexible coupler). The other flexible coupler (for example, the first flexible coupler) is provided with a preformed loop (first loop). After insertion of the fixation device within bone, the preformed loop of the first flexible coupler is passed through tissue to be secured to bone. The second flexible coupler is passed under the tissue and then passed through the preformed loop of the first flexible coupler, and then through an eyelet of the shuttle/pull device. The shuttle/pull device (suture passing instrument) is then pulled out of the fixation device to allow formation of a second loop which is a knotless, closed, adjustable, flexible, continuous loop.

The shuttle/pull device is provided attached to the second flexible coupler. The knotless self-locking mechanisms of the two flexible couplers allow the user (for example, the surgeon) to control the tension of each of the flexible couplers on the soft tissue (tendon, ligament, etc.) to be attached to bone. The flexible couplers may include any flexible material, strand or ribbon such as suture or tape or combinations thereof, for example, multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). The flexible coupler may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical constructs can be used with any type of flexible material or suture known in the art. The shuttle/pull device may be a shuttle/pull suture device such as a FiberLink™ or a Nitinol loop.

Methods of soft tissue repair which do not require tying of knots and allow adjustment of both the tension of the suture and the location of the tissue with respect to the bone, while providing self-locking, are also disclosed. An exemplary method comprises inter alia the steps of: (i) providing a surgical construct comprising a fixation device (for example, an anchor) with first and second self-locking, tensionable, knotless mechanisms, each including first and second flexible couplers (for example, suture) and with a shuttle/pull device (a suture passing instrument) attached to one of the flexible couplers; (ii) inserting the fixation device into bone; (iii) passing a preformed loop of one of the flexible couplers through tissue to be fixated (or reattached) to bone; (iv) passing the other flexible coupler through the preformed loop and then through an eyelet/loop of the shuttle/pull device; (v) subsequently, pulling on the shuttle/pull device to allow the other flexible coupler to pass through itself to form a splice and a knotless, closed, adjustable, flexible, continuous loop around the tissue; and (v) pulling on the first and second flexible couplers to adjust tension on the two loops (the preformed loop and the knotless, closed, adjustable, flexible, continuous loop) around tissue, to lock the construct, to allow the soft tissue to achieve the desired location relative to the bone, and to allow proper tensioning of the final construct.

The flexible couplers may be passed through at least a portion of the body of the fixation device (for example, through a full cannulation of the fixation device, or through a transversal opening at a distal end of the fixation device). Alternatively, the flexible couplers may be fixed to the fixation device (which may be solid or cannulated) by overmolding the coupler to the anchor body or by compressing the coupler against the bone (achieving an interference fit between the fixation device and the bone tunnel, compressing the flexible coupler).

Another exemplary method comprises inter alia the steps of: (i) securing a surgical construct to bone, the surgical construct comprising a fixation device (for example, an anchor) preloaded with a first flexible coupler (for example, suture) and a second flexible coupler (for example, suture), wherein one end of each flexible coupler is securely attached to the fixation device, and wherein one end of the first flexible coupler is spliced through itself and provided with a first splice and a first loop (preformed knotless, adjustable, closed, continuous loop with an adjustable perimeter), and the second flexible coupler is provided with a shuttle/pull device (a suture passing instrument) attached to the second flexible coupler; (ii) inserting the fixation device into bone; (iii) passing the first, preformed loop through tissue to be fixated or reattached to bone (for example, biceps); (iv) passing the second flexible coupler through the first loop and then through an eyelet/loop of the shuttle/pull device; (v) subsequently, pulling on the shuttle/pull device to allow the second flexible coupler to pass through itself to form a second splice and a second loop (a knotless, closed, adjustable, flexible, continuous loop with an adjustable perimeter) around the tissue (for example, biceps); and (v) pulling on the first and second flexible couplers to adjust tension on the first and second loops around tissue (for example, biceps), to lock the construct, to allow the tissue (for example, biceps) to achieve the desired location relative to the bone, and to allow proper tensioning of the final construct.

Referring now to the drawings, where like elements are designated by like reference numerals, FIGS. 1-17 illustrate exemplary surgical construct 100, 200, 300, 400 (surgical assembly 100, 200, 300, 400; surgical system 100, 200, 300, 400; tensionable, knotless construct 100, 200, 300, 400; tensionable, knotless, self-locking, surgical anchor 100, 200, 300, 400; double-loaded construct 100, 200, 300, 400) including exemplary fixation device 10, 210 with two exemplary knotless, self-locking, tensionable mechanisms 199, 299 within a body of the fixation device 10, 210.

Surgical construct 100 of FIG. 1 includes fixation device 10 preloaded with two exemplary knotless, self-locking, tensionable mechanisms 199, 299 formed by two separate flexible couplers 20, 120 (flexible strands 20, 120; sutures 20, 120). One of the two knotless, self-locking, tensionable mechanisms (for example, knotless, self-locking, tensionable mechanism 199) is formed of first flexible coupler 20 with a preformed loop 50 (pre-made loop 50; pre-assembled loop 50). The first flexible coupler 20 is also provided with two terminal ends, a first end 21 and a second end 23. The first end 21 is a fixed end that forms static knot 28 at the distal end 12, and the second end 23 is a flexible end that is pre-passed/spliced through the first flexible coupler 20 to form preformed loop 50 (first flexible, closed, knotless, continuous, adjustable loop 50) having an adjustable perimeter and adjustable length, and splice 55.

The other of the two knotless, self-locking, tensionable mechanisms (for example, knotless, self-locking, tensionable mechanism 299) is formed of second flexible coupler 120 with an attached shuttle/pull device 40 (suture passing instrument 40; suture passer 40). The second flexible coupler 120 is also provided with two terminal ends, a first end 121 and a second end 123. The first end 121 is a fixed end that forms static knot 128 at the distal end 12 of fixation device 10, and the second end 123 is a flexible end that is passed/spliced through the shuttle/pull device 40 at region splice 155 (to subsequently form a second flexible, closed, knotless, continuous, adjustable loop 150 having an adjustable perimeter and adjustable length, as detailed below). The shuttle/pull device 40 is a suture passing instrument or suture passer such as FiberLink™ 40 or a nitinol loop 40 attached to the flexible coupler 20 prior to formation of the second flexible, closed, knotless, continuous, adjustable loop. Suture passing device 40 includes an eyelet/loop 43 for passing the second flexible coupler 120.

Fixation device 10 is a tensionable knotless anchor having a hard anchor body 11 provided with a longitudinal axis 11*a*, a proximal end 13 and a distal end 12, and a plurality of ribs 15 extending circumferentially around it. Openings/channels allow threading flexible couplers and/or suture passing device(s) to pass around post 18, as detailed below. Cannulation 11*b* extends along the body 11 to allow passage of flexible couplers and of passing devices, as detailed below. A socket 19 may be provided at proximal end 13 and configured to securely engage a tip of a driver.

The openings/channels are positioned opposite to each other relative to the post 18 and also symmetrically located relative to the post 18, to allow flexible couplers 20, 120 (suture 20, 120) and shuttle/pull device 40 (suture passing instrument 40) shown in FIGS. 1-3 to pass and slide therethrough, as also detailed below. The openings/channels extend in a direction about perpendicular to the longitudinal axis 11*a*, and communicate through recesses with the outer surfaces 11*c* of anchor body 11. The position and size of the openings/channels and recesses may be determined according to the characteristics of the flexible couplers 20, 120 and shuttle/pull device 40, and of the arthroscopic procedure, and the need to precisely orientate the anchor during insertion to optimize suture tape sliding characteristics.

Fixation device 10 (anchor 10) may be a screw-in or a push-in style anchor. Fixation device 10 may be formed of metal, biocompatible plastic such as PEEK or a bioabsorbable PLLA material or a biocomposite material. Socket 19 at the proximal end 13 of the anchor 10 is configured to securely engage a tip of a driver, as detailed below. The socket of the fixation device 10 may have any shape adapted to receive a driver tip for pushing tap-in or screw-in style anchors. Tensionable knotless fixation device 10 may be made of one or more pieces, or may be provided as an integrated device. In an exemplary embodiment, fixation device 10 is a Corkscrew® anchor.

First and second flexible couplers 20, 120 are preloaded onto fixation device 10 by tying static knots 28, 128 which prevent flexible couplers 20, 120 from passing through distal blind hole 12*a*. The flexible couplers may also be preloaded by being molded into the anchor, for example, by insert molding or by any other means known in the art. Flexible couplers 20, 120 pass around post 18, which is large enough to allow the couplers to take gradual turns instead of sharp turns. Flexible couplers 20, 120 then pass through cannulation 11*b* and proximal blind hole 13*a*. Surgical construct 100 is loaded onto a driver (not shown), and the flexible couplers may be secured to the driver (for example, tied or wrapped around a cleft of the driver) to fasten the surgical construct securely to the driver.

Subsequent to the insertion of fixation device 10 of surgical construct 100 into a drilled hole in bone, the flexible couplers 20, 120 and suture passing device 40 are released from the driver, and the driver removed. Preformed loop 50 of first flexible coupler 20 is then passed through the tissue 80 which is to be reattached to bone 90. Free end 123 of second flexible coupler 120 is subsequently passed under the tissue 80 and through the preformed loop 50, and then through the eyelet/loop 43 of the suture passing device 40. Suture passing device 40 is then pulled, thereby pulling free end 123 of the second flexible coupler 120 towards the body of the fixation device. End 123 is further pulled into the fixation device so that it passes through itself, inside the fixation device, to form a splice 155 and another flexible, closed, knotless, continuous, adjustable loop 150. The suture passing device 40 has also been further pulled through second flexible coupler 120. FIG. 1 illustrates surgical construct 100 with second flexible coupler 120 before it has been pulled through the preformed loop 50 and through itself, and with suture passing device 40 that facilitates passing of the flexible coupler 120 through itself.

Reference is now made to FIGS. 2 and 3 which illustrate surgical construct 200 which is similar in part to surgical construct 100 of FIG. 1 in that it also includes exemplary knotless, self-locking, tensionable mechanisms 199, 299; however, construct 200 includes a soft fixation device 210 and not a hard fixation device 10, as in the embodiment of FIG. 1. Fixation device 210 may be in the form of a soft anchor (soft suture anchor, or all-suture soft knotless anchor) provided with a soft anchor sleeve 211 (sheath or tubular member 211) with two open ends 212, 213, and at least two flexible couplers 20, 120 (flexible strands 20, 120) extending through the soft anchor sleeve (sheath). The flexible couplers may extend through the sleeve in similar or different directions and/or orientations and/or locations. Details of an exemplary soft suture anchor with a soft anchor sleeve (sheath or tubular member) and flexible shuttling strands are set forth, for example, in U.S. application Ser. No. 15/998, 516 entitled "Methods of Tissue Repairs" filed on Aug. 16, 2018, the disclosure of which is incorporated by reference in its entirety herein.

First and second flexible couplers 20, 120 of FIGS. 2 and 3 also do not form any knots on the fixation device 210 but have rather free ends exiting the open ends 212, 213 of the sheath. First flexible coupler 20 is provided with end 21 exiting open end 212 of the sheath 210 and end 23 exiting open end 213, with preformed loop 50 and splice 55 residing within the body of the soft anchor. Similarly, second flexible coupler 120 has one end 121 exiting end 212 of the sheath and the other end 123 exiting the other open end 213 of the sheath. Shuttle/pull device 40 (suture passing instrument or suture passer such as FiberLink™ 40 or a nitinol loop 40) is attached to (passed through or spliced to) the second flexible coupler 120, with each end exiting a corresponding open end of the sheath. In an embodiment, shuttle/pull device 40 is spliced through the second flexible coupler 120 and exits the flexible coupler 120 at two separate locations A, B (entry and exit points A, B). In an embodiment, locations A, B are positioned fully within the body of the soft anchor sheath 210 and displaced from top surfaces of open ends 212, 213 of anchor sleeve 211, as shown in FIG. 2.

Surgical construct 300 is illustrated in FIG. 4. Surgical construct 300 is similar in part with surgical construct 100 depicted in FIG. 1 in that it also includes fixation device 10 attached to two flexible couplers 20, 120 with two exemplary knotless, self-locking, tensionable mechanisms 199, 299 within the fixation device. Surgical system 300 differs, however, in that it also includes an additional flexible coupler 25 (third coupler 25 or shuttle wire 25) connected to the preformed loop 50 of the first coupler 20. The third coupler 25 may be a simple suture or wire that is attached to the preformed loop 50 to allow further and easier manipulation of the first flexible coupler 20. For example, flexible coupler 25 can allow loading on a suture passer instrument, such as Scorpion™ suture passer, and easy pulling of the preformed loop while it is passed through tissue 80.

Figure 5:
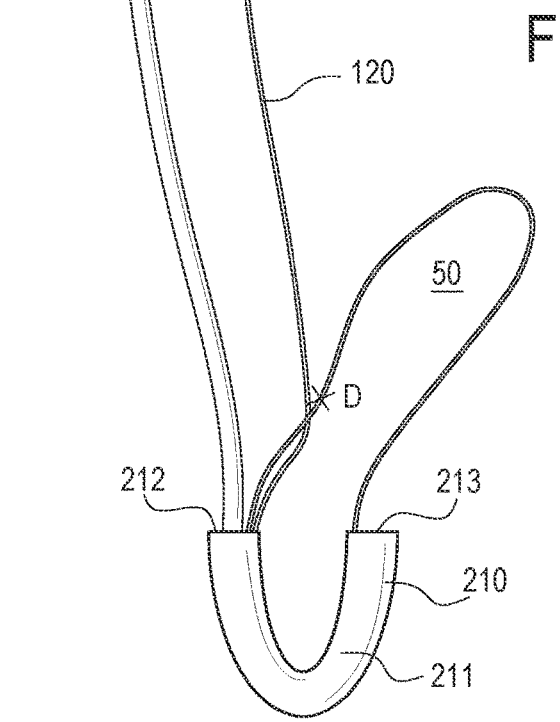
FIG. 5 illustrates a schematic view of a surgical construct according to yet another exemplary embodiment.

Surgical construct 400 is illustrated in FIG. 5. Surgical construct 400 is similar in part with surgical construct 200 depicted in FIGS. 2 and 3 in that it also includes fixation device 210 (soft anchor 210) attached to two flexible couplers 20, 120 with two exemplary knotless, self-locking, tensionable mechanisms 199, 299 within the fixation device. Surgical construct 400 differs, however, in that it also includes a slender tube 45 (a small, elongated diameter tube 45) that can be in the form of a simple straw 45. The straw allows a surgeon to temporarily hide the flexible couplers (sutures, strands, wires, etc.) until after the passing steps have been completed, to ease suture manipulation and to increase the visual field during the surgical procedure. If desired, an additional flexible coupler (such as the third flexible coupler 25 of FIG. 4) can be connected/attached to the preformed loop 50 of the first coupler 20, to further aid in suture manipulation. Slender tube 45 (straw 45) may be provided as part of a surgical kit or, alternatively, already pre-assembled with the surgical construct prior to surgeon's use during the specific surgical procedure.

Preformed loop 50 could be provided large enough to fit a cannula. Also, the preformed loop may be color-coded to differentiate from its pull stitch. For example, the preformed loop 50 could change color at point D along its perimeter (FIG. 5).

Figure 6:
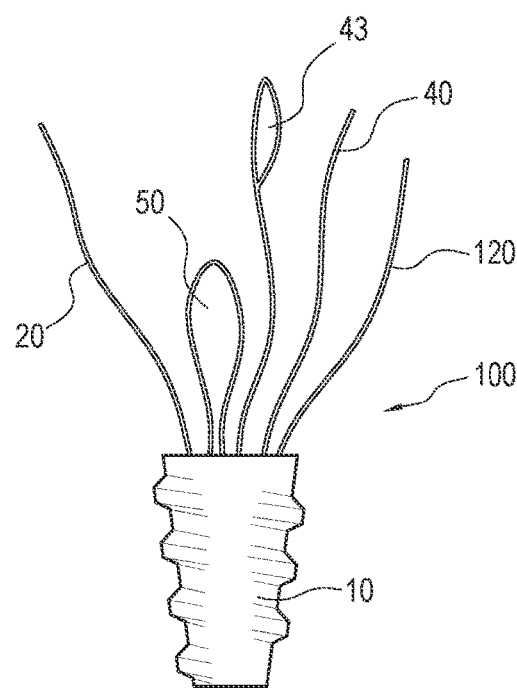
FIG. 6 illustrates a schematic view of the surgical construct of FIG. 1.

FIGS. 7-10 illustrate schematic steps of a tissue repair 101 (e.g., tendon or ligament repair) with the surgical construct 100 of FIG. 6 (which is a simplified depiction of the construct of FIG. 1, showing only the first and second flexible couplers 20, 120 with preformed loop 50 and shuttle/pull device 40). FIGS. 7-10 illustrate only a top view of tissue 80 (for example, tendon) to be secured to bone, and only schematic representations of the flexible couplers and associated elements of the construct 100 of FIG. 6. FIG. 7 illustrates tissue 80 before the passage of the preformed loop 50 through it. FIG. 8 illustrates preformed loop 50 already passed through the tissue 80.

Second flexible coupler 120 is then passed through the preformed loop 50 and then through the eyelet/loop 43 of the shuttle/pull device 40, as shown in FIG. 9. The shuttle/pull device 40 is then pulled out of the fixation device and out of the surgical site, to allow the second flexible coupler 120 to pass through itself and form a splice with a flexible, tensionable, continuous, adjustable, self-locking, cinching, closed loop 150 (FIG. 10) around tissue 80. Free end 23 of the first flexible coupler 20 can be also pulled in a direction away from the surgical site to allow the preformed loop 50 to be tensioned and to further secure the loop 150 to tissue 80 and form repair 101, as shown in FIG. 10.

Loops 50, 150 have an adjustable perimeter to allow tensioning of the final repair. When the ends are pulled, the construct shrinks, i.e., the perimeter of each of the loops decreases. Once the desired tension and location is achieved, the pulling ends may be clipped off to complete the soft tissue repair or fixation. In this manner, the flexible couplers 20, 120 are shuttled and pulled (during the surgery) to a desired tension and with the ability to securely lock the final repair/construct and achieve increased compression of tissue. When the user (surgeon) reduces slack, what is produced in the final repair is a Loop N' Tack™ repair.

Figure 11:
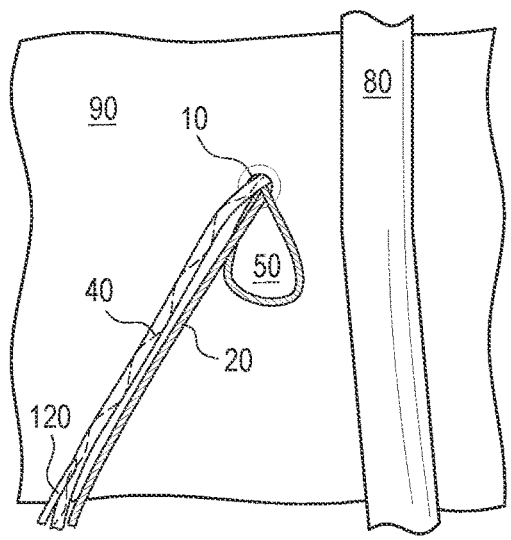
Figure 12:
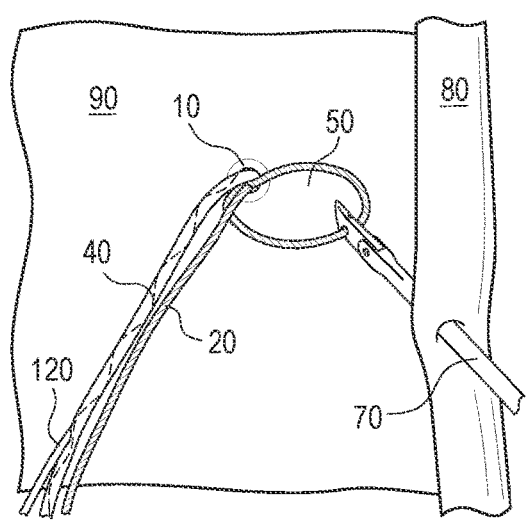
Figure 13:
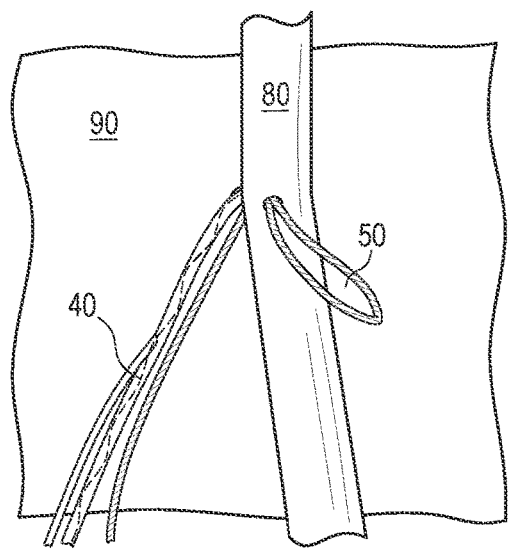

FIGS. 11-17 illustrate additional schematic steps of a tissue repair 201 with any of exemplary surgical constructs 100, 200, 300, 400. FIG. 11 illustrates exemplary fixation device 10 of surgical construct 100 inserted and secured within bone 90. Preformed loop 50 of first flexible coupler 20 resides on top of the bone 90 and adjacent tissue 80 (for example, tendon) to be attached to the bone. FIG. 12 illustrates instrument 70 inserted through the tissue 80 and grasping the preformed loop 50. FIG. 13 illustrates preformed loop 50 passed through the tissue 80. Instrument 70 may be any suture passing and retrieving instrument known in the art, for example, a KingFisher® Suture Retriever/Tissue Grasper instrument or a SutureLasso™ instrument.

Figure 14:
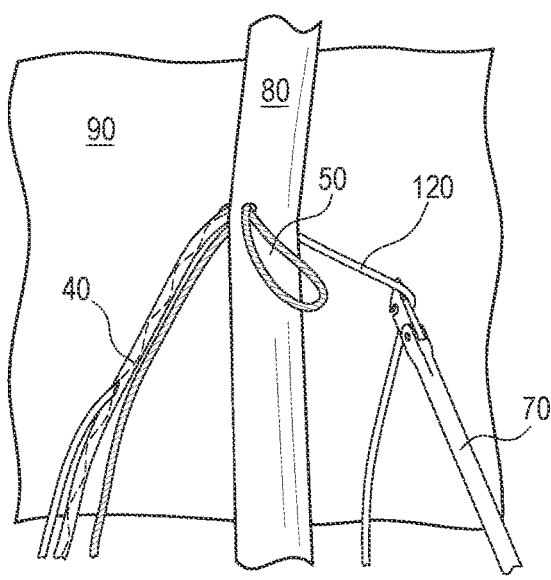

FIGS. 14 and 15 illustrate second flexible coupler 120 passed through the preformed loop 50 with the aid of instrument 70. The second flexible coupler 120 is subsequently passed through the eyelet/loop 43 of the attached shuttle/pull device 40. The shuttle/pull device 40 (with the second flexible coupler 120 passed through its eyelet 43) is then pulled out of the fixation device 10 and out of the surgical site and bone 90, to allow the second flexible coupler 120 to pass through itself and form splice 155 and a flexible, tensionable, continuous, adjustable, self-locking, cinching, closed loop 150 (FIG. 16) around tissue 80. The shuttle/pull device 40 has also been further pulled through second flexible coupler 120. FIG. 16 illustrates loop 150 connected to (intertwined with or passed through) preformed loop 50 as the second flexible coupler 120 was initially passed through it, and with the shuttle/pull device 40 removed. Loops 50, 150 both have an adjustable perimeter to allow tensioning of the final repair.

Free end 23 of the first flexible coupler 20 is pulled in a direction away from the bone and surgical site to allow the preformed loop 50 to shrink (decrease) and to be tensioned, while also further securing loop 150 to tissue 80. The free end 23 of flexible coupler 20 is pulled until the desired tension on the repair is achieved. When the surgeon reduces slack, what is produced is a Loop N' Tack™ stitch (luggage tag loop). After proper and final tensioning, ends of flexible couplers 20, 120 are clipped/removed to form knotless, tensionable repair 201, as shown in FIG. 17. The flexible couplers can be cut flush with a suture cutter instrument. Loops 50, 150 have an adjustable perimeter to allow tensioning of the final repair 201. The repair allows formation of a Loop 'N' Tack™ stitch with increased strength and compression to tendon 80.

The surgical construct may also come without a preloaded shuttle/pull device such as suture passing device 40, i.e., with the flexible, closed, knotless, continuous, adjustable preformed loop 50 already formed and with the second flexible coupler 120 having only a small loop at one of its ends. For example, a pre-assembled variation of the construct/implant may be used for a quick tenodesis application. Fixation device/anchor 10, 210 is inserted into bone 90; flexible, closed, knotless, continuous, adjustable loop 50 is passed through the tendon 80 and is pulled out of the tendon 80; a free end of the second flexible coupler 120 is passed through preformed loop 50 and through the small loop at its other end to form second, flexible, closed, knotless, continuous, adjustable loop 150 all around tendon 80 (around an outer perimeter of tendon 80); free end 23 of the first flexible coupler and free end of the second flexible coupler 120 are pulled to shrink the construct and the flexible, closed, knotless, continuous, adjustable loops 50, 150, and to compress the tendon to bone.

The constructs, systems, kits, and assemblies of the present disclosure may be employed in numerous knotless soft tissue repairs and fixations, for example, fixation of soft tissue to bone.

Although the embodiments above have been illustrated with reference to a double-loaded construct, the disclosure is not limited to these exemplary-only embodiments and contemplates knotless self-locking tensionable constructs that are multiple-loaded constructs, i.e., with three or more knotless self-locking tensionable mechanisms and three or more corresponding flexible couplers, to aid in increased tissue fixation and compression to bone.

The surgical constructs and methods of the present disclosure provide self-locking mechanisms, self-locking tensionable constructs and surgical constructs, as well as methods for tissue repair, for example, attachment of a first tissue to a second tissue, such as soft tissue to bone, with such constructs.

An exemplary method of tissue repair with surgical construct 100, 200, 300, 400 (including fixation device 10, 210; first and second flexible couplers 20, 120; and shuttle/pull device 40) comprises inter alia the steps of: (i) inserting fixation device 10, 210 into bone; (ii) passing a preformed loop 50 of one of the flexible couplers 20, 120 through tissue 80 to be fixated (or reattached) to bone 90; (iii) passing the other flexible coupler 120 through the preformed loop 50 and then through an eyelet/loop 43 of the shuttle/pull device 40; (iv) subsequently, pulling on the shuttle/pull device 40 to allow the other flexible coupler 120 to pass through itself to form a splice 155 and a knotless, closed, adjustable, flexible, continuous loop 150 around the tissue; and (v) pulling on the first and second flexible couplers 20, 120 to adjust tension on the preformed loop 50 and on the knotless, closed, adjustable, flexible, continuous loop 150 around tissue 80, to lock the construct, to allow the soft tissue 80 to achieve the desired location relative to the bone 90, and to allow proper tensioning of the final repair 101, 201.

Fixation device 10 may be an anchor formed of metal, biocompatible plastic such as PEEK or a bioabsorbable PLLA material or a biocomposite material. The anchor may be provided with a socket at the distal end (such as socket 19 of the anchor 10) configured to securely engage a tip of a driver. The socket of the anchor may have any shape adapted to receive a driver tip for pushing the anchors, for example, tap-in or screw-in style anchors. Tensionable knotless anchor 10 may be made of one or more pieces, or may be provided as an integrated device. In an exemplary embodiment only, the fixation device 10 is a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein. An exemplary knotless fixation device 10 comprises an anchor body (or screw) and an eyelet.

Flexible couplers 20, 120 may be in the form of any elongated members, fibers, or materials, or combinations thereof. Flexible couplers 20, 120 can include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

Flexible coupler 20, 120 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

Flexible coupler 20, 120 may include any flexible materials or strands such as suture or tape, for example, multifilament, braided, knitted, woven suture, or including fibers of ultrahigh molecular weight polyethylene (UHMWPE). The flexible couplers may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical self-locking constructs can be used with any type of flexible material or suture known in the art.

Flexible coupler 20, 120 may be also formed of a stiff material, or combination of stiff and flexible materials, particularly for the regions of the couplers that are passed/spliced through the body of the coupler and depending on whether they are employed with additional fixation devices. In addition, flexible couplers 20, 120 may be also coated and/or provided in different colors for easy manipulation during the surgical procedure. The knotless constructs and self-locking soft anchors of the present disclosure can be used with any type of flexible material or suture that may be weaved or passed through itself.

If desired, flexible coupler 20, 120 may be coated, impregnated, or otherwise stiffened with a material such as plastic, for example. Flexible couplers 20, 120 and/or passing device 40 may be also provided with tinted tracing strands, or otherwise contrast visually with the sheath of the construct, which remains a plain, solid color, or displays a different tracing pattern, for example. Various structural elements of surgical construct 100, 200, 300, 400 may be visually coded, making identification and handling of the suture legs simpler, Easy identification of suture in situ is advantageous in surgical procedures, particularly during arthroscopic surgeries, endoscopic and laparoscopic procedures.

Although the embodiments above have been described with reference to a particular embodiment, i.e., with flexible couplers 20, 120 forming tensionable self-locking mechanism 199, 299 (tensionable constructs 199, 299) within a body of the fixation device 10, 210, the disclosure has equal applicability to embodiments wherein the tensionable self-locking mechanisms 199, 299 (tensionable constructs 199, 299) are formed outside a body of the fixation device 10, 210. In addition, more than two flexible couplers may be pre-loaded or loaded onto fixation device 10, 210 and form more than two tensionable self-locking mechanisms 199, 299 (tensionable constructs 199, 299).

The disclosure provides a tensionable knotless Loop 'N' Tack™ construct and method for fixation of a biceps or similar tendon to bone. The anchor body could be a soft sheath, push in, or screw in anchor with a pre-made tensionable loop and a second knotless construct consisting of a repair suture with a knotless splice and a shuttling suture. The anchor is placed at the desired point of tendon fixation and the free repair suture is passed to the opposite side of the tendon. Then, a retriever is placed through the tendon to pull the pre-made tensionable loop through the biceps. Once pulled through, the retriever is placed through the loop to pull the free repair stitch through it. At this point, the free repair suture is passed through its knotless splice and tensioned. The pre-made loop is also tensioned to create the final repair construct.

The surgical construct (anchor) provides the ability to create an anchor first, tensionable, knotless Loop 'N' Tack™ construct with simple steps for quick repair of a biceps or similar tendon. It also provides the needed strength and compression for a tenodesis.

The disclosure provides a two-in-one knotless anchor system (i.e., two knotless anchors in one, or two knotless anchor mechanisms in one). One anchor is a pre-made (already formed or preformed) knotless fixation device with a loop and a splice. The other is a repair suture with a shuttling device attached to the repair suture. The anchors form two loops around the tissue to be fixated (tendon such as biceps) in a knotless, self-cinching, tensionable manner. The pre-made loop could have various dimensions to allow it, for example, to come out of a working cannula and so the surgeon could conduct the procedure out of the surgical site (for example, the joint), if necessary and desired.

The anchor system could be used either arthroscopically or in open procedures, open to tenodesis a tendon or ligament. The anchor system can be used with an elongate instrument such as a straw that hides some suture strands from the surgeon's visual field until the passing steps have been completed. Soft tissue 80 is luggage-tagged and secured to bone 90 with preformed loop 50 and loop 150 of the first and second flexible couplers 20, 120. A Loop 'N' Tack™ knotless tenodesis technique is an all-arthroscopic technique using the surgical constructs 100, 200, 300, 400. The constructs allow surgeons to conduct a Loop 'N' Tack™ stitch on a tendon with improved efficiency, improved tissue compression, and by eliminating multiple instruments necessary in open or arthroscopic procedures.

The surgical constructs of the present disclosure may be employed in endoscopic surgery. The term "endoscopic surgery" refers to surgical procedures within a patient's body through small openings as opposed to conventional open surgery through large incisions. Additionally, surgical constructs as disclosed herein may be utilized in other general surgical and specialty procedures that soft tissue repairs.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

The term "luggage tag stitch" is defined as any cinch or loop that is formed by the luggage tag technique.

What is claimed:

1. A method of knotless tissue repair comprising the steps of:
   securing a double-loaded fixation device into bone, the fixation device being preloaded with two independent, knotless, tensionable mechanisms, wherein one of the two independent, knotless, tensionable mechanisms includes a first flexible coupler with a first free end that is passed through itself to form a preformed loop, the preformed loop being a knotless, continuous, uninterrupted loop with an adjustable perimeter and an adjustable length,
   and wherein the other of the two independent, knotless, tensionable mechanisms includes a second flexible coupler with a knotless splice and a shuttle/pull device attached to the second flexible coupler;
   passing the preformed loop through soft tissue to be positioned relative to the bone;
   subsequently, passing a second free end of the second flexible coupler through the preformed loop and through a closed eyelet of the shuttle/pull device to form a knotless, closed, continuous loop around the soft tissue, wherein the knotless, closed, continuous loop is intertwined with the preformed loop and form a luggage-tag repair around the soft tissue; and
   pulling on the first free end of the first coupler and on the second free end of the second coupler to adjust tension on the preformed loop and on the knotless, closed, continuous loop, to allow the soft tissue to achieve a desired location relative to the bone.

2. The method of claim 1, further comprising the steps of pulling on the shuttle/pull device to allow the second flexible coupler to pass through itself to form another splice and the knotless, closed, continuous loop around the second tissue.

3. The method of claim 1, wherein the double-loaded fixation device is a hard-body anchor or a soft-body anchor.

4. The method of claim 1, wherein the double-loaded fixation device is a push-in anchor and each of the first and second flexible couplers is secured to the fixation device by a knot, and wherein the first and second flexible couplers and the shuttle/pull device extend through a body of the double-loaded fixation device.

5. The method of claim 1, wherein the soft tissue is tendon or ligament.

6. A method of forming a knotless, tensionable, self-locking repair, comprising:
   knotlessly attaching a first flexible coupler with a first free end and a second free end to a soft all-suture anchor, wherein the first flexible coupler is provided with a preformed loop, the preformed loop being a knotless, continuous, uninterrupted loop with an adjustable perimeter;
   knotlessly attaching a second flexible coupler with a first free end and a second free end to the soft all-suture anchor, wherein the second flexible coupler is attached to a shuttle/pull device;
   securing the soft all-suture anchor into a bone;
   passing the preformed loop through soft tissue to be approximated to the bone;
   subsequently, passing the second flexible coupler through the preformed loop;
   forming another loop with the second flexible coupler, the another loop being another knotless, continuous, uninterrupted loop with an adjustable perimeter, wherein the another loop is intertwined with the preformed loop; and
   pulling on the first flexible coupler and on the second flexible coupler to adjust tension of the preformed loop and the another loop, to approximate the soft tissue to the bone.

7. The method of claim 6, wherein the step of forming the another loop comprises:
   passing the second flexible coupler through a closed eyelet of the shuttle/pull device; and
   pulling the shuttle/pull device out of the soft all-suture anchor to form another splice and the another loop around the soft tissue.

8. The method of claim 6, wherein the preformed loop and the another loop form a luggage-tag repair around the second tissue.

9. The method of claim 1, further comprising the step of temporarily hiding the first and second flexible couplers within a slender tube in the form of a straw until the passing steps have been completed, to ease manipulation of the first and second flexible couplers and increase a visual field during the knotless tissue repair.

\* \* \* \* \*